United States Patent [19]

Smith et al.

[11] 4,155,916

[45] May 22, 1979

[54] FLUORESCENCE METHOD FOR ENZYME ANALYSIS WHICH COUPLES AROMATIC AMINES WITH AROMATIC ALDEHYDES

[76] Inventors: Robert E. Smith, 557 Escondido Cir.; Frank A. Dolbeare, 5178 Diane La., both of Livermore, Calif. 94550

[21] Appl. No.: 828,394

[22] Filed: Aug. 29, 1977

[51] Int. Cl.² .......................................... C07C 119/00
[52] U.S. Cl. .................................. 260/345.2; 560/21; 260/566 F; 195/103.5 R
[58] Field of Search .................. 260/566 F, 345.2; 560/21

[56] References Cited

U.S. PATENT DOCUMENTS

| | | | |
|---|---|---|---|
| 2,303,818 | 12/1942 | Cantrell et al. | 260/566 F |
| 3,041,165 | 6/1962 | Süs et al. | 260/566 F |
| 3,366,683 | 1/1968 | Johnson et al. | 260/566 F |
| 3,827,780 | 8/1974 | Labes | 260/566 F |
| 3,833,606 | 9/1974 | Mohan | 260/566 F |

OTHER PUBLICATIONS

Chemical Abstracts, vol. 71, 80,496 (v), (1969).
Chemical Abstracts, vol. 60, 4167 (e), (1964).
Chemical Abstracts, vol. 60, 14,469 (f), (1964).
Chemical Abstracts, vol. 12, 1880, (1918).

*Primary Examiner*—Gerald A. Schwartz
*Attorney, Agent, or Firm*—John C. McNett; Edward A. Figg

[57] ABSTRACT

Analysis of proteinases is accomplished using conventional amino acid containing aromatic amine substrates. Aromatic amines such as 4-methoxy-2-naphthylamine (4M2NA), 2-naphthylamine, aminoisophthalic acid dimethyl ester, p-nitroaniline, 5-methoxy-1-aminofluorene and coumarin derivatives resulting from enzymatic hydrolysis of the substrate couples with aromatic aldehydes such as 5-nitrosalicylaldehyde (5-NSA), benzaldehyde and p-nitrobenzaldehyde to produce Schiff-base complexes which are water insoluble. Certain Schiff-base complexes produce a shift from blue to orange-red (visible) fluorescence. Such complexes are useful in the assay of enzymes.

4 Claims, No Drawings

FLUORESCENCE METHOD FOR ENZYME ANALYSIS WHICH COUPLES AROMATIC AMINES WITH AROMATIC ALDEHYDES

BACKGROUND OF THE INVENTION

1. Field of the Invention

This invention relates to enzyme analysis and more particularly to a method for enzyme analysis with aromatic amines coupled to aromatic aldehydes.

2. Description of the Prior Art

One of the principles most widely used for colorimetrically demonstrating the presence of hydrolytic enzymes in tissue sections and homogenates involves the two step process:

(1) substrate $\xrightarrow{enzyme}$ coupling component + other products (2) coupling component + dye forming agent → dye.

The coupling components are aromatic hydroxy compounds or amines, usually of the naphthalene series. The dye forming agents are typically diazonium salts or other compounds which react in a similar manner with the coupling component to form a dye. The dyes formed when diazonium salts are used are azo dyes. One of the coupling components which has been used in histochemical localization of enzymes is 4-methoxy-2-napthylamine which was first made by Rosenblatt, Nachlas and Seligman (*Synthesis of m-Methoxynaphthylamines as precursors for Chromogenic Substrates,* 80 Jour. Am. Chem. Soc. 2463, July 1958). It was first used histochemically for the localization of enzymes wherein only one amino acid, y-Glutamyl, was attached. A. Rutenburg et al., *Histochemical and Ultrastructural Demonstration of y-Glutamyl Transpeptidase Activity,* 17 Jour. Histochemistry and Cytochemistry 517, 1969.

Carbobenzoxydiglycyl-1-arginyl-2-napthylamine hydrochloride was prepared by Plapinger et al. for the study of the enzyme trypsin. (*Synthesis of Chromogenic Arginine Derivatives as Substrates for Trypsin,* 30 Jour. of Organic Chem. 1871, June 1956). Carbobenzoxydiglycyl-1-arginyl-2-napthylamide as a trypsin substrate was used by Nachlas, Plapinger and Seligman, (*Role Of Some Structural Features of Substrates on Trypsin Activity,* 108 Archives of Biochemistry and Biophysics 266, 1964). While this compound is desirable because of its capability of facilitating the study of trypsin-like enzymes, its slow coupling rate with certain diazonium salts and lack of strong color of the coupled compound is an awkward and unwanted drawback.

Many of the prior art processes for determining enzyme concentrations have been based on amino acid derivatives of 2-napthylamine. (*Role of Some Structural Features of Substrates on Trypsin Activity, supra.*) Use of the 2-napthylamine coupling component in conjunction with a dye forming agent presents an inconveniently slow and relatively insensitive method for determining enzyme concentrations. Alternatively, the 2-napthylamine coupling component can be exposed to ultraviolet light and its fluorescence measured directly. While this eliminates problems associated with the use of a dye forming agent, the frequency of fluorescence (blue) is difficult to measure with inexpensive instruments and is similar to other materials often present in material being assayed.

U.S. Pat. No. 3,862,011 to Smith describes a colorimetric method for determining enzyme concentration in homogenates such as serum or tissue extracts employing 4-methoxy-2-napthylamines. To the homogenate is added an amino acid derivative of 4-methoxy-2-napthylamine (4M2NA) which acts as a substrate for a specific enzyme depending on the particular amino acid residue attached to the 4M2NA molecule. Enzymatic hydrolysis cleaves the arylamine bond to yield free 4M2NA which is then measured by azo coupling to an appropriate azo dye and thereafter using absorption photometry. Although not set forth in U.S. Pat. No. 3,862,011, 4M2NA has been known to be highly fluorescent, but with the undesirable blue color.

SUMMARY OF THE INVENTION

The present invention relates to the coupling of aromatic aldehydes such as benzaldehyde, p-nitrobenzaldehyde and 5-nitrosalicylaldehyde (5NSA) with aromatic amines such as 4M2NA, 2-napthylamine, aminoisophthalic acid dimethylester, p-nitroaniline, 5-methoxy-1-aminofluorene and certain coumarin derivatives to form Schiff-base complexes which are water insoluble and produce fluorescent compounds. For example, the 5NSA/4M2NA complex is easy to detect due to the orange-red color of its fluorescence. Also the ultraviolet absorption spectrum of the coupled 5NSA/4M2NA matches more closely the wavelength of commonly available lasers. The formed 5NSA/4M2NA complex in addition to being an insoluble product due to the 5NSA also shifts the peak of fluorescence emission of 4M2NA from 425 nm to 595 nm.

One embodiment of the invention involves a method of assaying enzymes that hydrolyses an arylamide bond. In this method one adds to an unknown to be tested for an enzyme, a suitable amino acid containing, aromatic amine substrate and a suitable aromatic aldehyde. The mixture is incubated to allow for hydrolysis of the substrate by the enzyme. After incubation, fluorescence of the mixture is observed.

DESCRIPTION OF THE PREFERRED EMBODIMENT

This invention first provides a novel method for evaluating enzymatic activity such as in intact cells or in sonicated call suspensions. This is made possible by aromatic aldehydes, such as p-nitrobenzaldehyde, benzaldehyde and 5-nitrosalicylaldehyde, that form highly insoluble, yet usually fluorescent complexes with aromatic amines. In assaying intact cells, these complexes are retained within the cell. Proteolytic enzyme activities in single cells are measured by microfluorophotometry or in a group of cells by flow cytometry. With this information, different cell types can be analyzed, separating mixed cell populations by their different enzyme activities.

The aromatic amines referred to herein are formed in conventional fashion by the enzymatic hydrolysis of conventional amino acid containing water dispersible aromatic amine substrates well known in the art. No novelty is claimed herein to the selection of a particular aromatic amine substrate for a particular enzyme. Similarly, the aromatic aldehydes referred to herein may be any one of a large number of water dispersible aromatic aldehydes which are suitable for coupling to the hydrolyzed aromatic amine. Aromatic aldehydes are preferred to be 5-nitrosalicylaldehyde, benzaldehyde or p-nitrobenzaldehyde. Other aromatic aldehydes include, for example, naphthaldehydes, dimethylaminobenzaldehyde, anisaldehyde, piperonal and bromobenzaldehydes. Lower molecular weights are preferred to improve water dispersability.

The complex which forms between the amide and the aldehyde is believed to include a double bond between the N of the amine and the C of the aldehyde. The N of the amine is then left with no H bonded to it and the C of the aldehyde with only one H. One molecule of water is believed produced in the formation of the complex.

The complexes do not quench the fluorescence of the napthylamine, but rather shift the fluorescence to a longer wavelength.

This invention also provides a method for flow cytometric analysis or proteinases in single cells by coupling certain aromatic amines such as 4-methoxy-2-naphthylamine (4M2NA) with aromatic aldehydes such as 5-nitrosalicylaldehyde (5NSA) to give a shift in fluorescence from blue to orange-red.

A substrate is suspended in a buffer and vortexed to form a solution to which is added 5NSA. Single cell fluorescence is then measured in cells by the deposition of an insoluble reaction product which consists of a complex of liberated 4M2NA and the 5NSA.

Practical and presently preferred embodiments of the present invention will be illustrated in the following examples:

EXAMPLE I 100 mg. 5NSA is dissolved in a few drops of dimethyl formamide diluted with 0.1 M sodium acetate buffer to 1 liter volume and vortexed for 20 seconds to produce a solution. A second solution of substrate comprising leucine 4-methoxy-2-naphthylamine in the presence of morpholinethanesulfonic acid (MES) buffer (pH 7.2) is prepared. The two solutions are mixed to achieve in the resulting solution 0.1 $\mu$mol of substrate and 0.33 $\mu$mol of 5NSA per 100 $\mu$l of solution. This solution is mixed with mouse embryo fibroblasts (Balb3T3 cells) and incubated for 45 minutes at 20° C. In an assay for amino peptidase, the solution is then exposed to 420 nm excitation frequency and read at 590 nm. The assay results were highly accurate and sensitive when compared to a control.

EXAMPLE II

To a 1 mmol. per liter buffered solution at pH 5.6 of lys-ala-4M2NA is added an equal volume of a solution of 3 mmol. per liter 5NSA. To this combined solution is added dissociated anterior pituitary cells from a rat, incubated for 15 minutes at 37° C., washed with cold buffer near neutrality. The enzyme is subsequently assayed by using the excitation frequency of 420 nm and emission frequency of 590 nm. The formed compound is a complex of liberated 4M2NA with 5NSA. The result is the localization of the yellowish orange fluorescence reaction product for the enzyme DAP-2 within the pituitary cells.

EXAMPLE III

A substrate glutaryl-ala-ala-ala-4M2NA is made up in a buffer solution at neutrality with a concentration of one mmol. per liter. This is added to an equal quantity of 5-nitrosalicylaldehyde solution containing 4 mmol. per liter. To this is added the buffie coat of white blood cells. It is incubated for 10 minutes at 37° C. The liberated 4M2NA complexes with the 5NSA and the fluorescence is observed as in the preceding examples. The effect is to localize and assay for the enzyme elastase.

EXAMPLE IV

The procedure of Example III was followed except that the 5NSA was added after incubation. While the localization of the enzyme is poor with this approach, a valid quantitative assay of the enzyme was achieved.

EXAMPLES V-X

Various substrates shown below are made up in buffer solutions with concentrations of 1 mmol. per liter. To these were added equal volumes of a solution of 5NSA containing 3 mmol. per liter. Quantitative assays of the enzymes were determined by fluorescence as in Example I:

Pro-arg-4M2NA (pH 6 assay of rat liver cells) assayed for Cathepsin C.

Leucine-2-naphthylamine (pH 7.2 assay of intestinal villus/cells) assayed for Leucine Aminopeptidase.

Carbobenzoxy-ala-arg-arg-4M2NA assayed for Cathepsin $B_1$.

Gammaglutamylaminoisophthalic acid dimethyl ester (pH 8.5 assay of kidney cells) assayed for glutamic acid transferase.

Benzarg-p-nitroaniline (pH 7.8 assay of pancrease) assayed for trypsin-like enzymes.

Glutarylglyglyphe-7-amino-4-methylcoumarin (pH 7.0 assay of neutrophiles) assayed for chymotrypsin-like enzymes (known as cathepsin G).

EXAMPLES XI-XVII

The procedures of Examples I and V-X were followed substituting benzaldehyde for the 5NSA. While the coupling reaction was somewhat slower, the flourescence was more reddish. Accurate quantitative assays were achieved.

EXAMPLES XVIII-XXIV

The procedures of Example I and V-X were followed substituting p-nitrobenzaldehyde for the 5NSA. Acceptable results were achieved.

EXAMPLES XXV-XXIX

The procedure of Example I was followed substituting naphthaldehyde, anisaldehyde, dimethylaminobenzaldehyde, piperonal, and bromobenzaldehyde for the 5NSA. While coupling rates were slower, and aqueous dispersal difficult to achieve in certain cases, all functioned to form an insoluble complex useful for localizing and assaying for the enzyme leucine aminopeptidase.

A useful trapping agent for quantitative cytochemistry must be soluble, diffuse easily into cells, and react with released product fast enough to prevent its diffusion from the cell; yet it must not be a potent inhibitor of the enzyme-substrate reaction. The reaction is faster at a lower pH, and the reaction rate is increased about 20% by increasing the temperature from 20° C. to 37° C. Equilibrium of the coupling reaction is also pH dependent.

The inhibitory effect of 5NSA on arylamidase activity is best demonstrated by measuring initial hydrolytic rates with and without added 5NSA. Carbobenzoxy-arg-arg-4M2NA hydrolysis and Lys-Ala-4M2NA activity are not affected significantly by 1 mmol/liter 5NSA, a concentration well above that required for complete trapping of the liberated 4M2NA within the cell. At 10 mmol/liter, 50% inhibition of all enzyme activities occurs. Interfering side reactions with 5NSA may occur.

The compound reacts with both aliphatic and aromatic amine groups to form Schiff-Base complexes. Particularly susceptible are proteins containing lysine and glutamine. Lysine at a concentration of 1 mmol/liter, however, does not inhibit or interfere with formation of the 4M2NA/5NSA complex at pH 4 to 7. Derivatives having leucine or proline as the n-terminal amino acid do not react with 5NSA. Cell proteins react at higher concentrations, i.e., above 1 mmol/liter of 5NSA, to form a blue-green fluorescence, which may account for as much as 15% of the cellular fluorescence at 530nm. Use of appropriate filters to block out green fluorescence will block out the nonspecific cell protein reaction with 5NSA.

Amino acid derivative of aromatic amines, preferrably 4M2NA, can be used to evaluate arylamidase activity such as in intact cells or sonicated cell suspensions. This is made possible by use of an aromatic aldehyde, preferrably 5NSA, that is water dispersible, yet forms highly insoluble and usually fluorescent complexes that are retained within the cell. Proteolytic enzyme activities in single cells are measured by microfluorophotometry or in a group of cells by flow microfluorometry. With this technique, different cell types can be analyzed, separating mixed cell populations by their different enzyme activities.

The simultaneous coupling of a product of a proteolytic reaction and 5NSA or similar aromatic aldehyde is limited to a pH below 7.0. However, coupling is possible after completion of the enzymatic reaction when the product (e.g., aromatic amines) is less soluble and remains in the cell at a more alkaline pH. Other trapping methods have been employed to retain a product within the cell such as lead in phosphatase assays, diazonium salts to trap phenols in esterase reactions, and Rhodamine 6G with a lead salt to trap the homovanillic acid dimer after peroxidase reaction. Most of these methods have been used to form dense or opaque precipitates to permit absorption measurements on cells. Only the homovanillic acid-Rhodamine 6G method provides a fluorescent product deposited within the cell. Most coupling reactions, however, quench the fluorescence of the product, e.g., diazonium salts and the naphthols. Schiff-base formation does not quench the fluorescence of naphthylamines or aminocoumarins, but rather shifts the fluorescence to a longer wavelength. The presence of the methoxy group on the naphthylamine not only enhances the insolubility of the reaction product, but also results in a fluorescence at a longer wavelength than that of 5NSA complexing with 2-naphthylamine.

While particular embodiments of the invention have been described for the purpose of illustration, it should be understood that only the preferred embodiments have been described in detail.

What is claimed is:

1. A compound of the formula

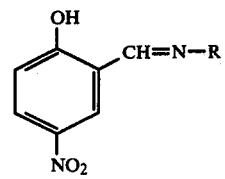

in which R is selected from the group consisting of

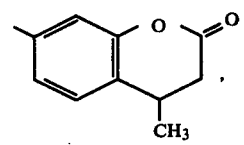,

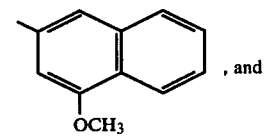, and

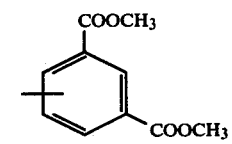.

2. The compound of claim 1 wherein R is

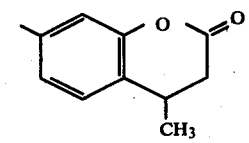

3. The compound of claim 1 wherein R is

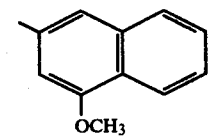

4. The compound of claim 1 wherein R is

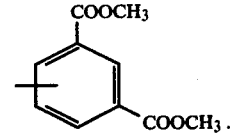.

* * * * *